(12) United States Patent
Osborn et al.

(10) Patent No.: US 12,303,479 B2
(45) Date of Patent: May 20, 2025

(54) CHLORIDE INTRACELLULAR CHANNEL 1 FOR REGULATION OF FOOD INTAKE

(71) Applicant: The Regents of the University of California, Oakland, CA (US)

(72) Inventors: Olivia Osborn, Cardiff, CA (US); Rizaldy Zapata, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 767 days.

(21) Appl. No.: 17/608,837

(22) PCT Filed: May 6, 2020

(86) PCT No.: PCT/US2020/031570
§ 371 (c)(1),
(2) Date: Nov. 4, 2021

(87) PCT Pub. No.: WO2020/227344
PCT Pub. Date: Nov. 12, 2020

(65) Prior Publication Data
US 2022/0313636 A1    Oct. 6, 2022

Related U.S. Application Data

(60) Provisional application No. 62/843,862, filed on May 6, 2019.

(51) Int. Cl.
| | |
|---|---|
| *A61K 31/192* | (2006.01) |
| *A61K 31/155* | (2006.01) |
| *A61K 31/365* | (2006.01) |
| *A61K 31/47* | (2006.01) |
| *A61K 31/57* | (2006.01) |
| *A61K 31/704* | (2006.01) |

(52) U.S. Cl.
CPC .......... *A61K 31/192* (2013.01); *A61K 31/155* (2013.01); *A61K 31/365* (2013.01); *A61K 31/47* (2013.01); *A61K 31/57* (2013.01); *A61K 31/704* (2013.01)

(58) Field of Classification Search
None
See application file for complete search history.

(56) References Cited

U.S. PATENT DOCUMENTS

| | | | |
|---|---|---|---|
| 2002/0065325 A1 | 5/2002 | Lamb et al. | |
| 2008/0312286 A1 | 12/2008 | Pinkerton et al. | |
| 2009/0069437 A1* | 3/2009 | Gluskin | A61P 3/04 514/635 |
| 2010/0168030 A1 | 7/2010 | Zoltani et al. | |
| 2014/0024683 A1 | 1/2014 | Emala et al. | |

FOREIGN PATENT DOCUMENTS

KR    10-2014-0130655    * 11/2014 ............... A61K 8/97

OTHER PUBLICATIONS

Tang et al., "CLICs-dependent chloride efflux is an essential and proximal upstream event for NLRP3 inflammasome activation" Nature Communications, 2017, vol. 8: 202, pp. 1-12.

Esser et al., "Obesity phenotype is related to NLRP3 inflammasome activity and immunological profile of visceral adipose tissue" Diabetologia, 2013, vol. 56, pp. 2487-2497.

Wang et al., "Identification of Potent Chloride Intracellular Channel Protein 1 Inhibitors from Traditional Chinese Medicine through Structure-Based Virtual Screening and Molecular Dynamics Analysis" Hindawi BioMed Research International, 2017, vol. 2017, pp. 10.

PCT, "International Search Report and Written Opinion" App. No. PCT/US2020/031570 mailed Sep. 10, 2020; pp. 10.

* cited by examiner

*Primary Examiner* — Dale R Miller
(74) *Attorney, Agent, or Firm* — Eversheds-Sutherland (US) LLP

(57) ABSTRACT

Compositions and methods of use for modulating weight gain in a subject. Methods for treating obesity in a subject comprising administering to a subject in need an effective amount of a chloride intracellular channel protein 1 (Clic1) inhibitor, such as indanyloxyacetic acid 94 (IAA94).

10 Claims, 9 Drawing Sheets

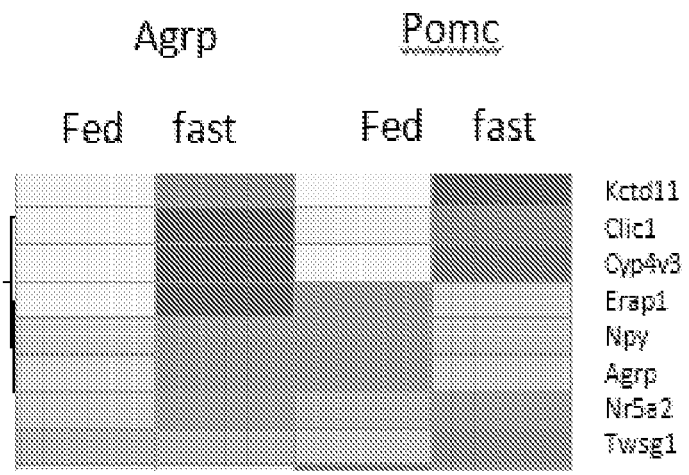
Figure 1A
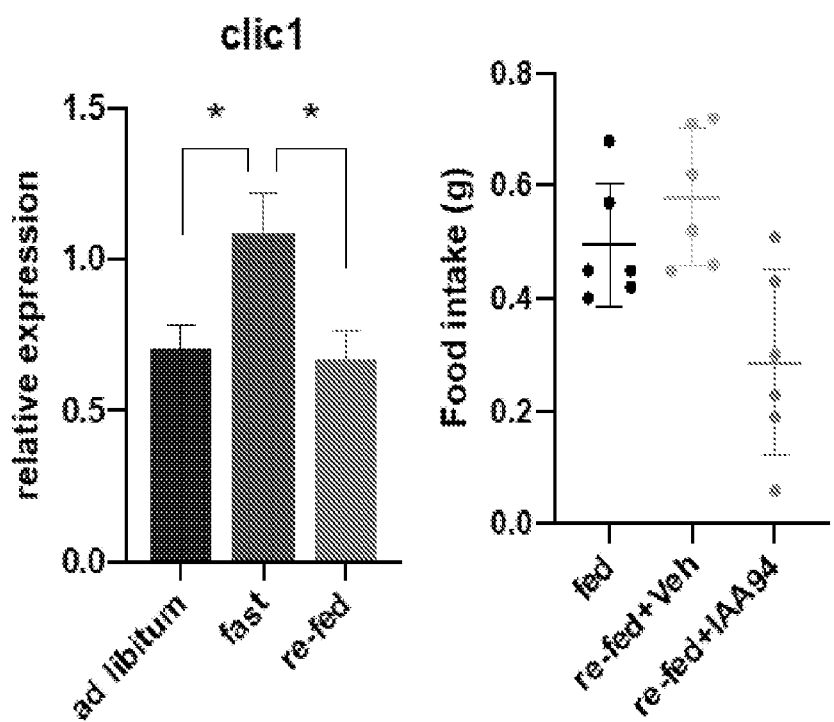
Figure 1B
Figure 1C

CHLORIDE INTRACELLULAR CHANNEL 1 FOR REGULATION OF FOOD INTAKE

CROSS REFERENCE TO RELATED APPLICATIONS

This application claims the priority benefit of PCT/US2020/227344 filed on May 6, 2020, which claims the priority benefit of U.S. Provisional Application No. 62/843,862, filed May 6, 2019, which applications are incorporated herein by reference.

GOVERNMENT SPONSORSHIP

This invention was made with government support under grant No. DK117872 awarded by the National Institutes of Health. The government has certain rights in the invention.

TECHNICAL FIELD

The present invention relates to therapeutic targets for regulation of food intake.

BACKGROUND

It is well-known that atypical antipsychotic drugs used to treat psychiatric conditions also have dominant side effects of increased food intake and weight gain in both rodent and human studies[1,2]. However, the underlying mechanisms driving hyperphagia remain unknown. Previous studies have identified that minocycline co-treatment blocks antipsychotic-induced hyperphagia and weight gain in mice, and the hypothalamic pathways controlling food intake in mice has been elucidated[3].

Previously, atypical antipsychotics have been used in the treatment of anorexia nervosa[4-7] and cachexia[8,9]. However, in practice, a major limitation of this approach is that even when antipsychotics are effective in increasing food intake in these patients, they also have mood dampening effects that can be highly disadvantageous in some patients.

Therefore, there is a need to identify more specific targets and therapies that can be used to modulate food intake for treating hyperphagia for example, or alternatively for treating cachexia for example, and other conditions of patients in need.

SUMMARY OF THE INVENTION

The present invention provides methods of inhibiting weight gain or treating hyperphagia or obesity in a subject comprising administering to a subject in need an effective amount of a chloride intracellular channel protein 1 (Clic1) inhibitor or antagonist.

In embodiments, the invention provides methods of inhibiting weight gain or treating hyperphagia or obesity, wherein the Clic1 inhibitor or antagonist decreases expression of Clic1.

In embodiments, the invention provides methods of inhibiting weight gain or treating hyperphagia or obesity, wherein the Clic1 inhibitor or antagonist decreases activity of Clic1.

In embodiments, the invention provides methods of inhibiting weight gain or treating hyperphagia or obesity, wherein the Clic1 inhibitor or antagonist is IAA94.

The present invention provides methods of increasing weight in a subject comprising administering to a subject in need an effective amount of a chloride intracellular channel protein 1 (Clic1) inducer or agonist.

In embodiments, the invention provides methods of increasing weight, wherein the subject has anorexia or cancer-induced cachexia. In embodiments, the invention provides methods of treating cachexia in a subject comprising administering to a subject in need an effective amount of a chloride intracellular channel protein 1 (Clic1) inducer or agonist.

In embodiments, the present invention provides pharmaceutical compositions for use in inhibiting weight gain, hyperphagia or obesity comprising a Clic1 inhibitor or antagonist of Clic1 and a pharmaceutically acceptable carrier. In embodiments, the present invention provides pharmaceutical compositions for use in promoting weight gain comprising a Clic1 inducer or agonist and a pharmaceutically acceptable carrier.

BRIEF DESCRIPTION OF THE DRAWINGS

FIGS. 1A-1C show the role of Clic1 in food intake.

DETAILED DESCRIPTION

Figures 2A, 2B, 2C, 2D:
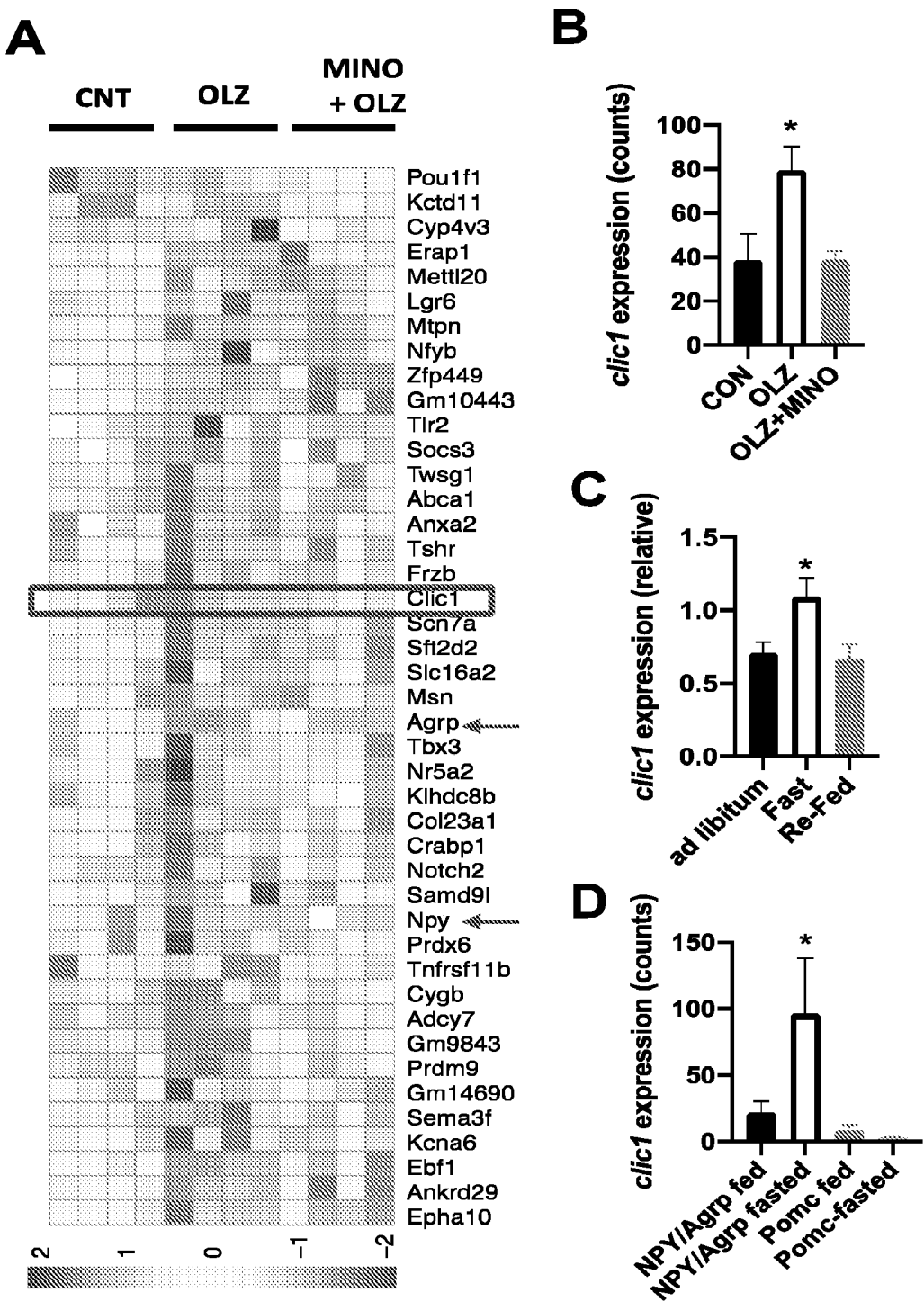
FIGS. 2A-2D show hypothalamic expression of Clic1.

All publications, patents, and patent applications mentioned in this specification are herein incorporated by reference to the same extent as if each individual publication, patent, or patent application was specifically and individually indicated to be incorporated by reference. Publications are intended to refer to the most current edition available at the present time.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{nd}$ ed., (Pharmaceutical Press and Philadelphia College of Pharmacy at University of the Sciences 2012).

The present invention provides methods of inhibiting appetite, hunger, weight gain or treating hyperphagia or obesity in a subject comprising administering to a subject in need an effective amount of a chloride intracellular channel protein 1 (Clic1) inhibitor or antagonist.

In embodiments, the invention provides methods of inhibiting appetite, hunger, weight gain or treating hyperphagia or obesity, wherein the Clic1 inhibitor or antagonist decreases expression of Clic1.

In embodiments, the invention provides methods of inhibiting appetite, hunger, weight gain or treating hyperphagia or obesity, wherein the Clic1 inhibitor or antagonist decreases activity of Clic1.

In embodiments, the invention provides methods of inhibiting appetite, hunger, weight gain or treating hyperphagia or obesity, wherein the Clic1 inhibitor decreases activity of Clic1 and is IAA94, and derivatives thereof. IAA94 is also known as indanyloxyacetic acid 94, or R(+)-Methylindazone, or R(+)-[(6,7-Dichloro-2-cyclopentyl-2,3-dihydro-2-methyl-1-oxo-1H-inden-5-yl)-oxy]acetic acid, and is commercially available (for example from Sigma-Aldrich). The structure of IAA94 is shown below:

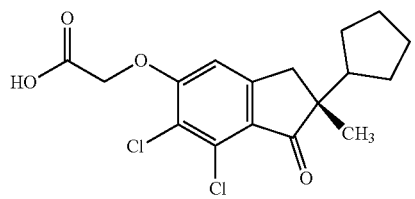 [SMILES: C[C@]1(C2CCCC2)Cc2cc(OCC(=O)O)c(Cl)c(Cl)c2C1=O]

In embodiments, the Clic1 inhibitor is metformin (N,N-dimethylbiguanide). In embodiments, the Clic1 inhibitor or antagonist can be other small molecules, an antibody or an aptamer.

In embodiments, the Clic1 inhibitor is selected from compound 2 compound 14, compound 16, compound 20, compound 22, and compound 24, and derivatives thereof as defined below[28]:

Compound 2

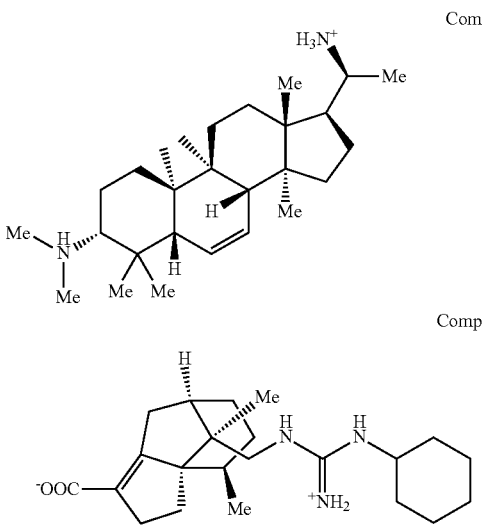

Compound 14

Compound 16

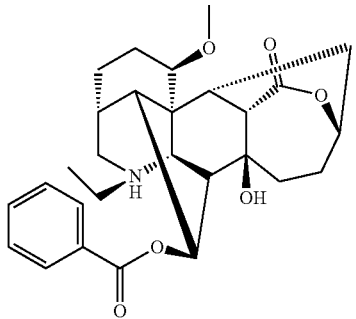

Compound 20

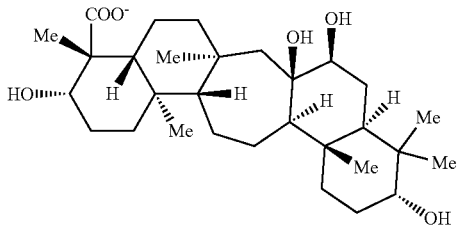

Compound 22

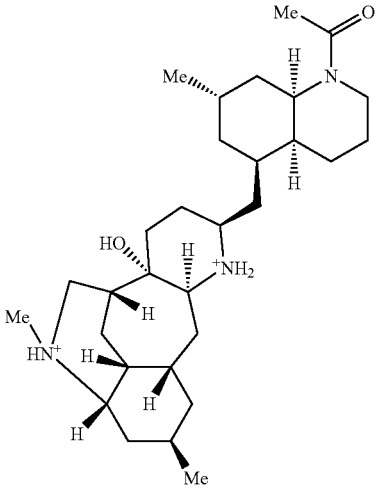

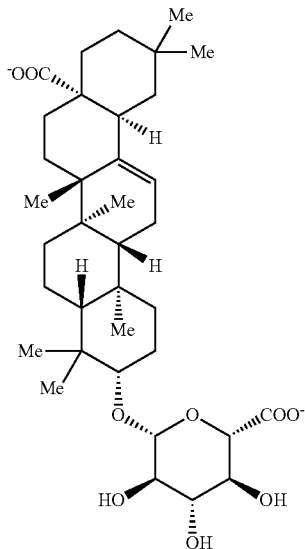

Compound 24

The present invention provides methods of increasing appetite, hunger, food intake or weight in a subject comprising administering to a subject in need an effective amount of a chloride intracellular channel protein 1 (Clic1) inducer or agonist. In embodiments, the Clic1 inducer or agonist can be Clic1 protein, a Clic1 gene, a small molecule, an antibody or an aptamer.

In embodiments, the invention provides methods of increasing appetite, hunger, food intake or weight in a subject, wherein the Clic1 inducer or agonist increases expression of Clic1. In embodiments, the invention provides methods of the invention provides methods of increasing appetite, hunger, food intake or weight in a subject, wherein the Clic1 inducer or agonist increases activity of Clic1.

In embodiments, the invention provides methods of increasing appetite, hunger, or weight, wherein the subject has anorexia or cancer-induced cachexia. In embodiments, the invention provides methods of treating cachexia in a subject comprising administering to a subject in need an effective amount of a chloride intracellular channel protein 1 (Clic1) inducer or agonist.

In embodiments, the present invention provides pharmaceutical compositions for use in inhibiting appetite, hunger, weight gain, hyperphagia or obesity comprising a Clic1 inhibitor or antagonist of Clic1 and a pharmaceutically acceptable carrier. In embodiments, the present invention provides pharmaceutical compositions for use in promoting appetite, hunger, or weight gain comprising a Clic1 inducer or agonist and a pharmaceutically acceptable carrier.

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a protein, a pharmaceutical composition, and/or a method that "comprises" a list of elements (e.g., components, features, or steps) is not necessarily limited to only those elements (or components or steps), but may include other elements (or components or steps) not expressly listed or inherent to the protein, pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to a pharmaceutical acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent. As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

The term "antibody" as used herein encompasses monoclonal antibodies (including full length monoclonal antibodies), polyclonal antibodies, multi-specific antibodies (e.g., bi-specific antibodies), and antibody fragments so long as they exhibit the desired biological activity of binding to a target antigenic site and its isoforms of interest. The term "antibody fragments" comprise a portion of a full length antibody, generally the antigen binding or variable region thereof. The term "antibody" as used herein encompasses any antibodies derived from any species and resources, including but not limited to, human antibody, rat antibody, mouse antibody, rabbit antibody, and so on, and can be synthetically made or naturally-occurring.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The "monoclonal antibodies" may also be isolated from phage antibody libraries using the techniques known in the art.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art.

The invention may also refer to any oligonucleotides (antisense oligonucleotide agents), polynucleotides (e.g. therapeutic DNA), ribozymes, DNA aptamers, dsRNAs, siRNA, RNAi, and/or gene therapy vectors. The term "antisense oligonucleotide agent" refers to short synthetic segments of DNA or RNA, usually referred to as oligonucleotides, which are designed to be complementary to a sequence of a specific mRNA to inhibit the translation of the targeted mRNA by binding to a unique sequence segment on the mRNA. Antisense oligonucleotides are often developed and used in the antisense technology. The term "antisense technology" refers to a drug-discovery and development technique that involves design and use of synthetic oligonucleotides complementary to a target mRNA to inhibit production of specific disease-causing proteins. Antisense technology permits design of drugs, called antisense oligonucleotides, which intervene at the genetic level and inhibit the production of disease-associated proteins. Antisense oligonucleotide agents are developed based on genetic information.

As an alternative to antisense oligonucleotide agents, ribozymes or double stranded RNA (dsRNA), RNA interference (RNAi), and/or small interfering RNA (siRNA), can also be used as therapeutic agents for regulation of gene expression in cells. As used herein, the term "ribozyme" refers to a catalytic RNA-based enzyme with ribonuclease activity that is capable of cleaving a single-stranded nucleic acid, such as an mRNA, to which it has a complementary region. Ribozymes can be used to catalytically cleave target mRNA transcripts to thereby inhibit translation of target mRNA. The term "dsRNA," as used herein, refers to RNA hybrids comprising two strands of RNA. The dsRNAs can be linear or circular in structure. The dsRNA may comprise ribonucleotides, ribonucleotide analogs, such as 2'-O-methyl ribosyl residues, or combinations thereof. The term "RNAi" refers to RNA interference or post-transcriptional gene silencing (PTGS). The term "siRNA" refers to small dsRNA molecules (e.g., 21-23 nucleotides) that are the mediators of the RNAi effects. RNAi is induced by the introduction of long dsRNA (up to 1-2 kb) produced by in vitro transcription, and has been successfully used to reduce gene expression in variety of organisms. In mammalian cells, RNAi uses siRNA (e.g. 22 nucleotides long) to bind to the RNA-induced silencing complex (RISC), which then binds to any matching mRNA sequence to degrade target mRNA, thus, silences the gene.

These and other embodiments of the invention will become apparent to those skilled in the art in view of the non-limiting exemplary methods and compositions described herein.

EXAMPLES

The present invention identified six genes (Kctd11, Cyp4v3, Erap1, NR5a2, Twsg1 and Clic1, see FIG. 1A), including chloride intracellular channel 1 (Clic1), that tracked closely with expression of pro-feeding peptides Agrp and Npy and that were also differentially expressed between the fasted and fed states. Hypothalamic gene expression of Clic1 was measured in mice in ad libitum fed, 24 hr fasted and 23 hr fasted mice and then re-fed for 1 hour. Clic1 expression was significantly induced in the hypothalamus during the fasted state and expression returned to equivalent ad libitum levels upon re-feeding. The invention provides that genes implicated in increased food intake can be targeted in the context of obesity, and reciprocally can also be modulated in the opposite direction to increase food intake in subjects in need, such as those suffering from anorexia or cachexia.

To determine whether the modulation of Clic1 directly affected food intake, mice were treated with a specific Clic1 inhibitor, IAA94[11]. Mice were fasted for 23 hours and then treated with either vehicle or IAA94 (50 mg/kg IP) and then re-fed for 1 hour. Clic1 inhibition significantly reduced food intake by approximately ~50% compared with vehicle treated mice and this was associated with significant reduction in hypothalamic levels of Npy and increased Pomc expression. No changes in AgRP or Cart expression were detected.

Cancer-induced anorexia is mediated by activation of calcitonin gene-related peptide (CGRP) neurons in the parabrachial nucleus (PBN)[12]. These neurons are activated by visceral signals that suppress feeding and are inhibited by hunger promoting hypothalamic AgRP/Npy neurons[13,14]. A novel role of Clic1 expression in AgRP/Npy neurons in the regulation of food intake was discovered. Expression of Clic1 increases in the fasted state and may contribute to the pro-feeding response. Conversely, inhibition of Clic1 reduced food intake and was associated with increased expression of satiety associated peptide Pomc and decreased expression of pro-feeding peptide Npy. Therefore, logically increasing expression of Clic1 plays a role in promoting food intake.

Clic1 is a relatively small 241 amino acid ion channel with a single transmembrane region and is particularly unusual as it exists in both soluble and membrane-associated forms. Changes in cellular pH and oxidative stress[16] are believed to trigger Clic1 proteins to transform from their predominant glutathione-S transferase (GST)-like structure soluble form[17] to that of an integral membrane protein[18]. Clic1 is expressed ubiquitously in human tissues and is highly expressed in immune cells (biogps.gnf.org). Clic1 participates in inflammatory processes by regulating macrophage phagosomal functions such as pH and proteolysis[11,19]. These data all point to an important role for Clic1 in regulating macrophage function through its ion channel activity and suggest it is a suitable target for the development of anti-inflammatory drugs[11]. Clic1 is also expressed in the brain and Clic1 inhibition may be beneficial in neurodegenerative disease[20] by preventing neuronal apoptosis and inhibiting TNF alpha release[21].

Recently it has been shown that metformin also inhibits Clic1[22] and thus it is possible that Clic1 inhibition may contribute to the weight loss effects of metformin. Furthermore, Clic1 KO mice are viable and fertile[23] and notably are protected from development of arthritis[11]. However, Clic1 is also involved in the regulation of cell cycle, cell proliferation and differentiation and its expression is increased in many cancers[24-26]. While downregulation of Clic1 results in inhibition of cell proliferation in vitro and in vivo[27], systemic upregulation of Clic1 could likely lead to tumor cell proliferation, invasion, and metastasis. Interestingly, some reports suggest that inhibitors could be specific for the enzymatic or channel form[17] which may have different effects on cell proliferation. Furthermore, pharmaceutical compositions can be localized to the hypothalamus or most preferentially the arcuate nucleus, to overcome these potential tumorigenic implications in cancer patients. Alternatively, inhibition of Clic1 can be used to promote satiety, thereby inhibiting weight gain and promoting weight loss, in a subject.

FIGS. 1A-1C show the role of Clic1 in food intake. FIG. 1A shows the extraction of RNA seq data from raw data from Henry et al., 2015. These data suggest Clic1 is localized in AgRP neurons which are the "pro-feeding" neurons and expression of Clic1 increases in the fasted state. FIG. 1B shows that expression of Clic1 increases in the hypothalamus in response to fasting and decreases after re-feeding in mice. FIG. 1C shows that inhibition of Clic1, by IAA94 (50 mg/kg) results in decreased hyperphagia in response to refeeding.

FIGS. 2A-2D show hypothalamic expression of Clic1. FIG. 2A shows RNA-seq signature of hypothalamic genes specifically induced by olanzapine (OLZ) and blocked by minocycline (MINO) co-treatment (APIGXS) n=4 per group, q<0.3, q value, which is the smallest false discovery rate at which a gene is deemed differentially expressed. FIG. 2B shows hypothalamic expression of Clic1 in control, olanzapine and olanzapine+Minocycline treated mice. FIG. 2C shows hypothalamic expression of Clic1 in in ad libitum fed, 24 hr fasted and 23 hr fasted mice and then re-fed for 1 hour. FIG. 2D shows expression of Clic1 in AgRP and Pomc neurons, using RNA seq data from Henry et al., 2015. P<0.05 One-way ANOVA with Sidak's multiple comparisons test.

Figure 3:
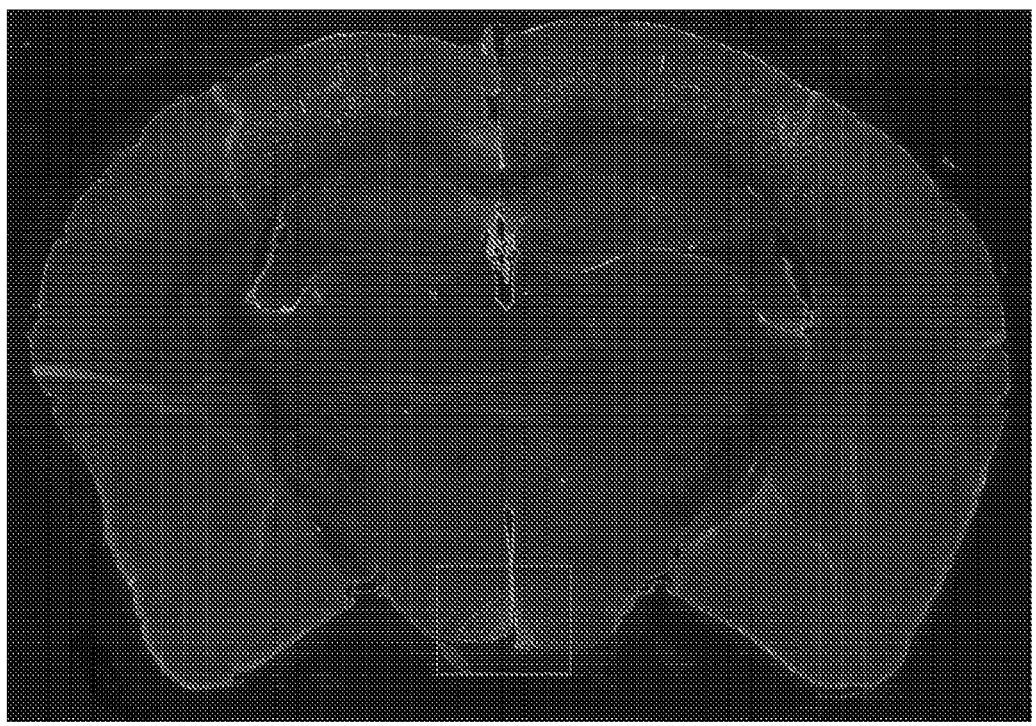
FIG. 3 shows Clic1 expression in ARC in a mouse brain.

FIG. 3 shows Clic1 expression in ARC in a mouse brain. IHC with Clic1 antibody (sc-374202) 1:1000 dilution, Secondary antibody goat-anti-mouse IgG, (Alexa Fluor 488) ab150113(1:1000).

Figure 4A:
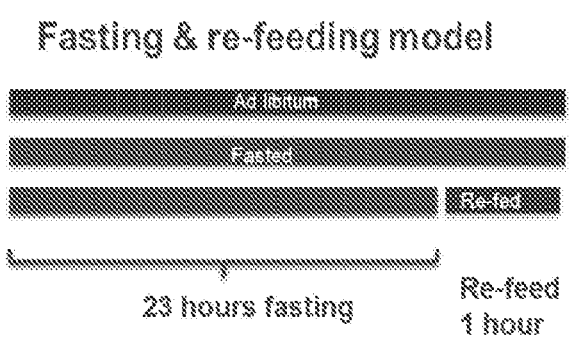
FIGS. 4A-4B show hypothalamic expression of Clic1 increases in fasted state and decreases after re-feeding.
Figure 4B:
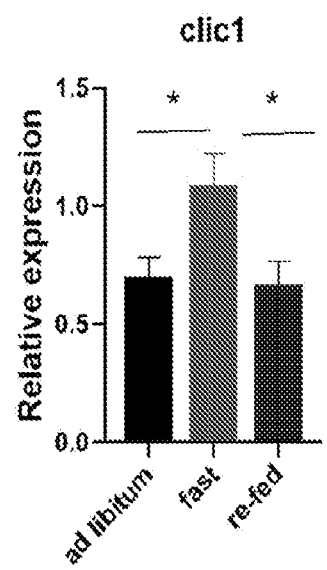

FIGS. 4A-4B show hypothalamic expression of Clic1 increases in fasted state and decreases after re-feeding. FIG. 4A shows the fasting and re-feeding model. FIG. 4B shows expression of Clic1 increases in the hypothalamus in response to 24 hour fasting and upon re-feeding for 1 hour expression returns to equivalent ad libitum fed levels in mice. P<0.05 One-way ANOVA with Sidak's multiple comparisons test.

Figure 5A:
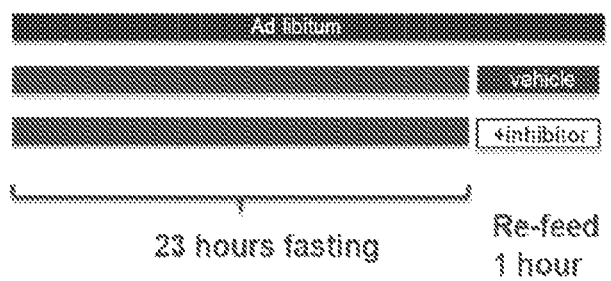
FIGS. 5A-5C show Clic1 inhibition decreases food intake.
Figure 5B:
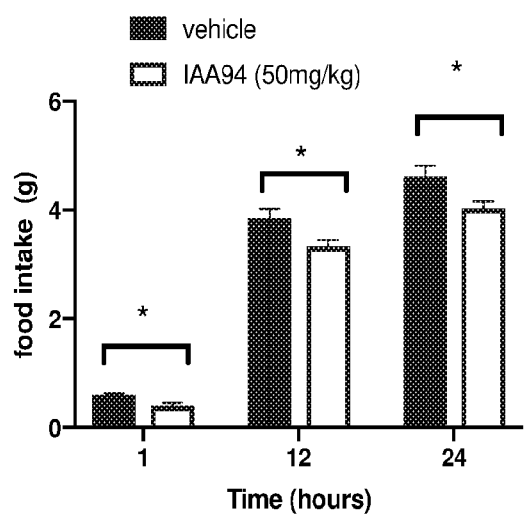
Figure 5C:
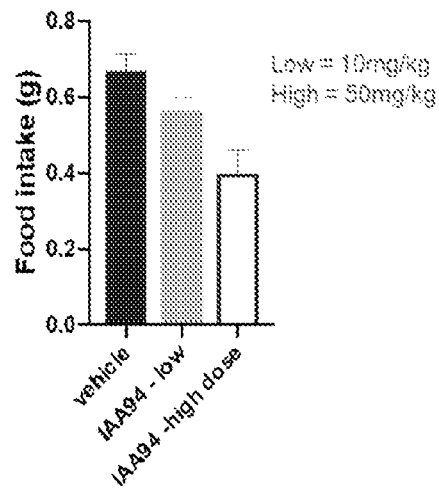

FIGS. 5A-5C show acute studies in which Clic1 inhibition decreases food intake. HET/KO mice are viable, fertile and appear normal. Floxed mice are available at PMID: 20049953 Sydney. FIG. 5A shows the fasting and re-feeding model. Male mice were injected with IAA94 (50 mg/kg) or vehicle and then refed. IAA94 (indanyloxyacetic acid 94) is a Clic1 inhibitor that blocks channels and has enzymatic properties. FIG. 5B shows the effect over time. FIG. 5C shows that food intake is dose dependent on the amount of IAA94 administered.

Figure 6A:
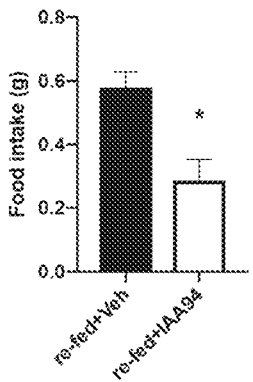
FIGS. 6A-6C show that Clic1 inhibition decreases food intake and is associated with decreased Npy and increased Pomc expression.
Figure 6B:
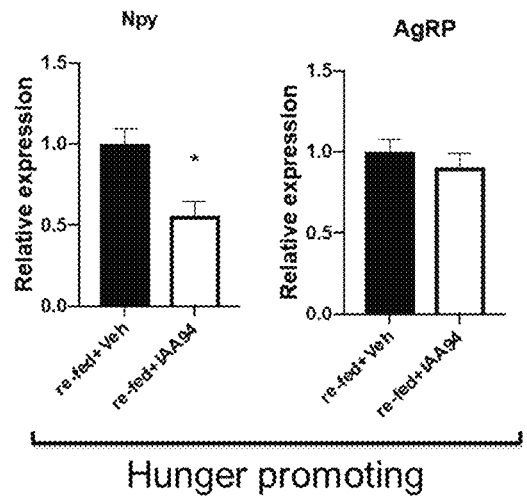
Figure 6C:
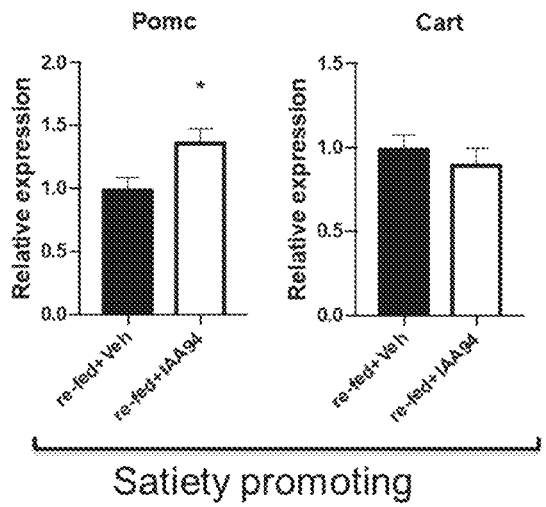

FIGS. 6A-6C show that Clic1 inhibition decreases food intake and is associated with decreased Npy and increased Pomc expression.

Figures 7A, 7B, 7C, 7D, 7E, 7F, 7G, 7H, 7I, 7J:
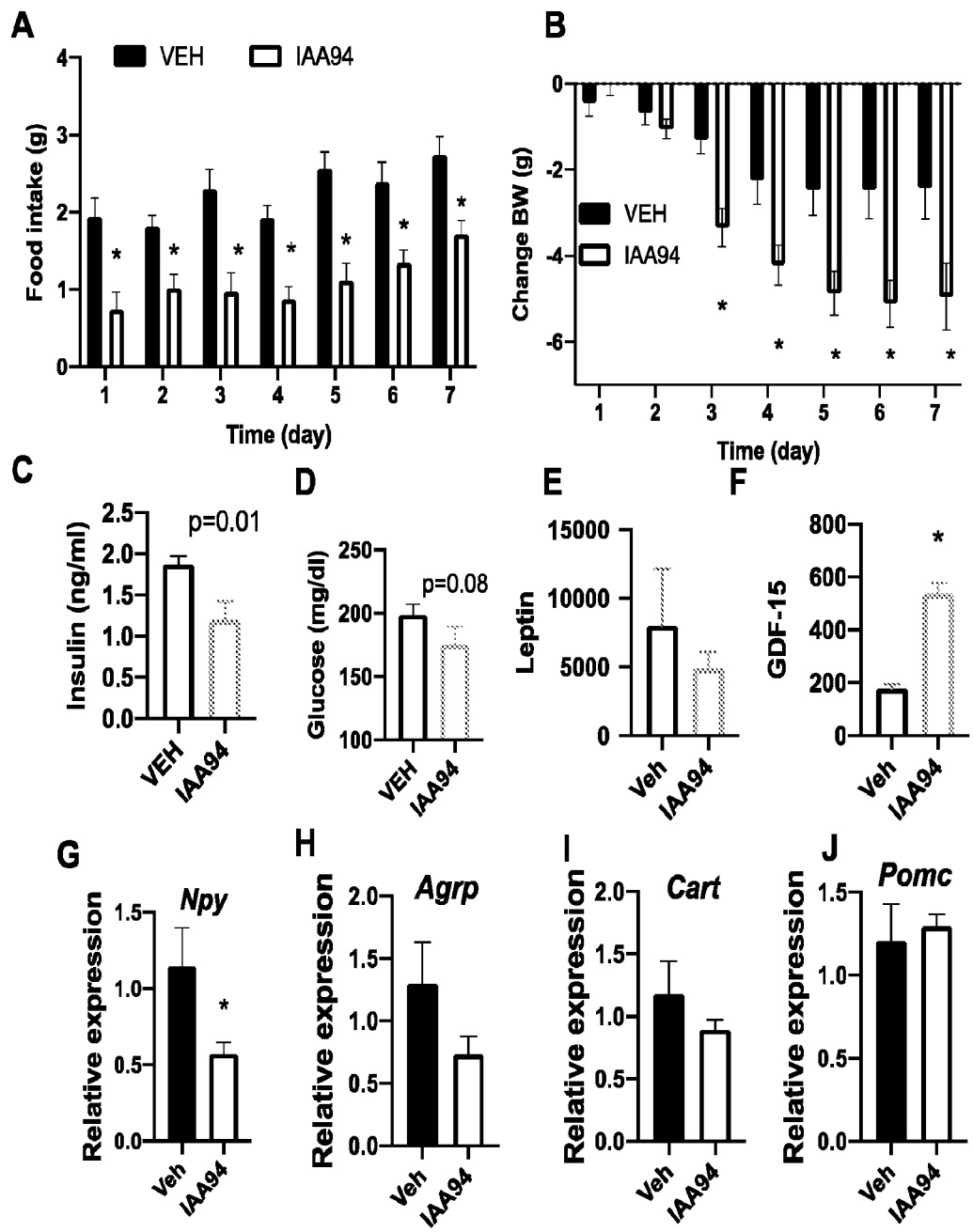
FIGS. 7A-7J show chronic Clic1 inhibition results in significant reduction in food intake and body weight loss in C57B16 WT high fat diet-fed mice.

FIGS. 7A-7J show chronic Clic1 inhibition results in significant reduction in food intake and body weight loss in C57Bl6 WT high fat diet-fed mice. Diet-induced obese mice (fed high fat diet for 6 weeks) were injected with IAA94 (50 mg/kg, IP, daily) or vehicle. Their daily food intake and body weight were monitored. Sacrifices were performed on day 7. FIG. 7A shows food intake. FIG. 7B shows change in body weight, in obese mice fed high fat diet for 6 weeks and then treated with IAA94 (50 mg/kg, IP) or vehicle (Saline+4% DMSO, 10% TWEEN80) daily for 7 days. On day 7 mice were fasted for 5 hours and then treated with IAA94 or VEH and then blood collected one hour later for measurement of leptin (FIG. 7C) GDF-15 (FIG. 7D) insulin (FIG. 7E), and glucose (FIG. 7F). FIGS. 7G-7J show hypothalamic neuropeptide levels determined by quantitative PCR detection. In FIGS. 7A-7B, P<0.05 repeated measures one-way ANOVA with Sidak's multiple comparisons test. In FIGS. 7C-7J, P<0.05 students t-test. Overall, Clic1 inhibition significantly reduced body weight by ~12% in one week.

Figure 8A:
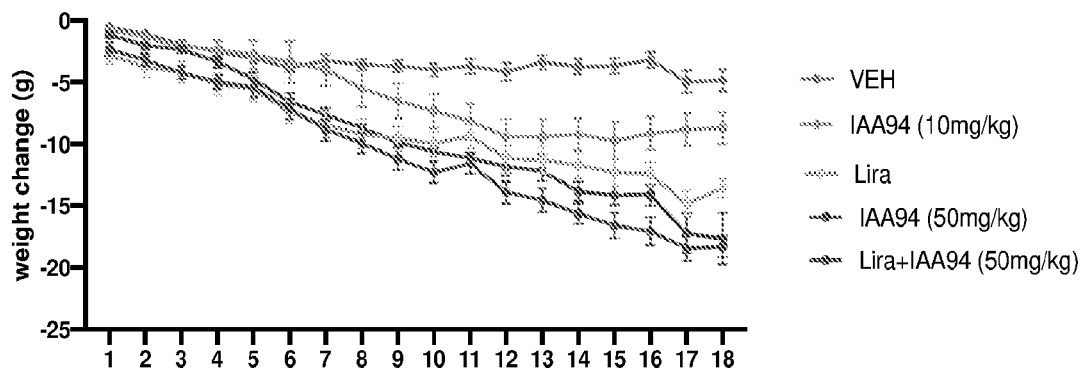
FIGS. 8A-8I show the effects of chronic IAA94 treatment.
Figure 8B:
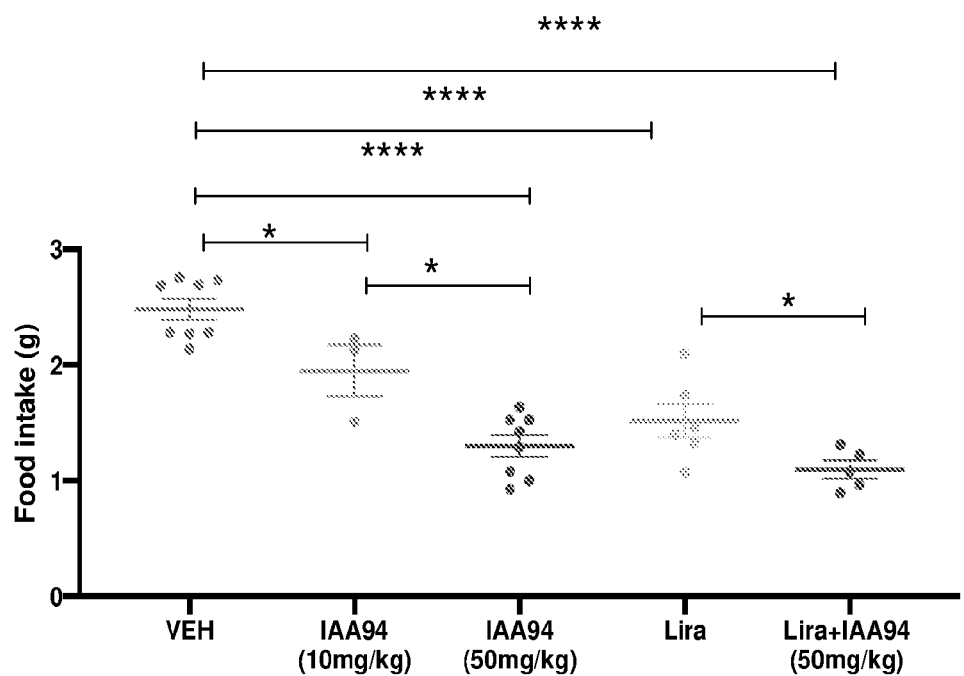
Figure 8C:
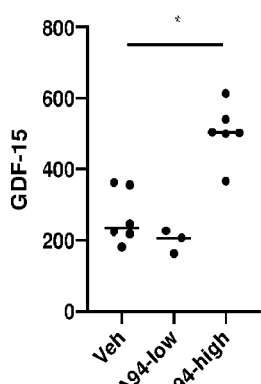
Figure 8D:
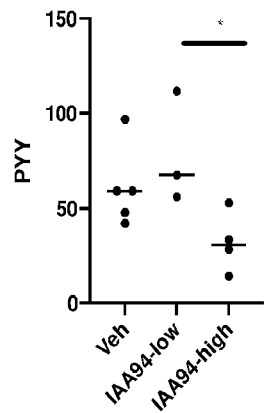
Figure 8E:
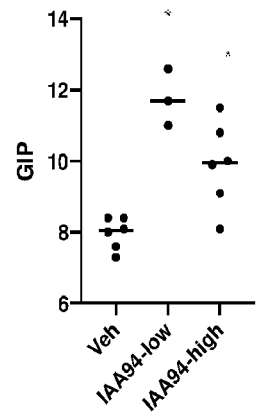
Figure 8F:
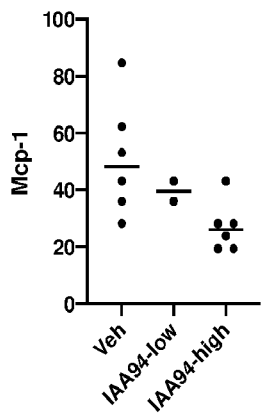
Figure 8G:
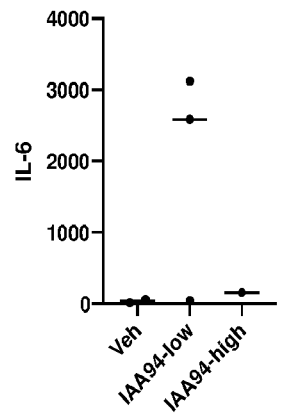
Figure 8H:
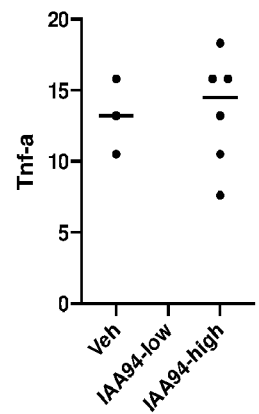
Figure 8I:
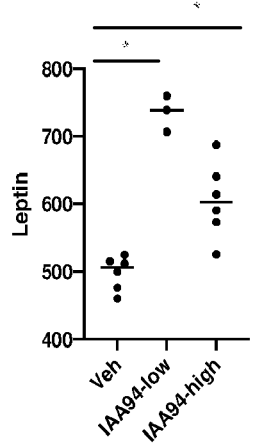

FIGS. 8A-8I show another study on chronic IAA94 treatment. Diet-induced obese mice (fed a high fat diet for 6 weeks) received daily injections of either i) vehicle, ii) IAA94—10 mg/kg, iii) IAA94—50 mg/kg, iv) Lira, or v) combination of Lira+IAA94 (50 mg/kg). Daily food intake and body weight were monitored. Sacrifices were performed after 23 days. FIG. 8A shows that chronic treatment with IAA94 results in significant weight loss (grayscale). At day 18, the most significant weight loss was seen in Lira+IAA94 (50 mg/kg), IAA94 (50 mg/kg), Lira, IAA94 (10 mg/kg), and vehicle respectively. FIG. 8B shows the average daily food intake. FIG. 8C shows changes in peripheral signals implicated in food intake.

Figures 9A, 9B, 9C:
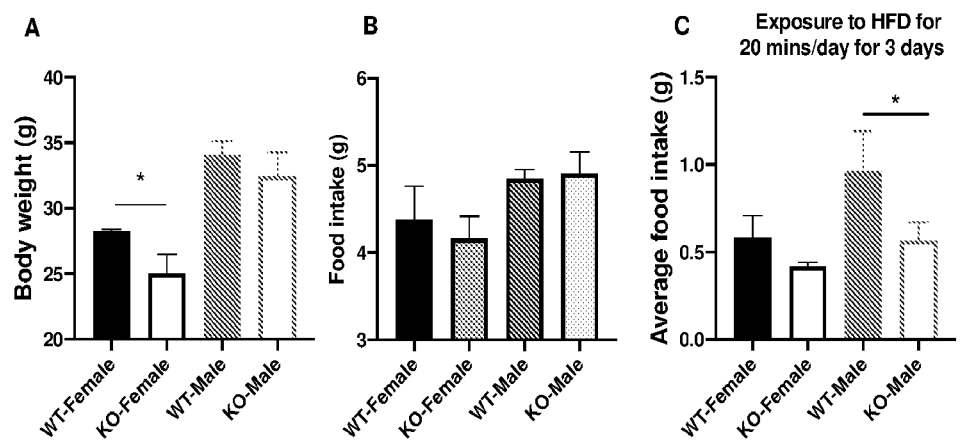
FIGS. 9A-9C show a Clic1 whole body KO mouse phenotype.

FIGS. 9A-9C show a Clic1 whole body KO mouse phenotype. Food intake and body weight in normal chow fed mice was studied. As shown in previous studies female Clic1 knockout (KO) mice, fed normal chow, are significantly leaner than WT littermates. The body weight effect is less pronounced in male mice, but the trend of lower body weight in KO compared with WT is still present. Female KO mice fed normal chow eat slightly less than WT littermates, but this trend is not significant.

When exposed to 45% HFD for just 20 minutes a day, KO mice show less motivation/drive to consume the novel food, despite its palatability, and eat significantly less than WT mice.

REFERENCES

1 Fountaine, R. J. et al. Increased food intake and energy expenditure following administration of olanzapine to healthy men. *Obesity (Silver Spring)* 18, 1646-1651, doi:10.1038/oby.2010.6 (2010).

2 Mathews, J. et al. Neural correlates of weight gain with olanzapine. *Arch Gen Psychiatry* 69, 1226-1237, doi: 10.1001/archgenpsychiatry.2012.934 (2012).

3 Perez-Gomez, A. et al. A phenotypic *Caenorhabditis elegans* screen identifies a selective suppressor of antipsychotic-induced hyperphagia. *Nat Commun* 9, 5272, doi:10.1038/s41467-018-07684-y (2018).

4 Bissada, H., Tasca, G. A., Barber, A. M. & Bradwejn, J. Olanzapine in the treatment of low body weight and obsessive thinking in women with anorexia nervosa: a randomized, double-blind, placebo-controlled trial. *Am J Psychiatry* 165, 1281-1288, doi:10.1176/appi.ajp.2008.07121900 (2008).

5 Brambilla, F. et al. Olanzapine therapy in anorexia nervosa: psychobiological effects. *Int Clin Psychopharmacol* 22, 197-204, doi:10.1097/YIC.0b013e328080ca31 (2007).

6 Marzola, E. et al. Atypical antipsychotics as augmentation therapy in anorexia nervosa. *PLoS One* 10, e0125569, doi:10.1371/journal.pone.0125569 (2015).

7 Mondraty, N. et al. Randomized controlled trial of olanzapine in the treatment of cognitions in anorexia nervosa. *Australas Psychiatry* 13, 72-75, doi:10.1080/j.1440-1665.2004.02154.x (2005).

8 Naing, A. et al. Olanzapine for cachexia in patients with advanced cancer: an exploratory study of effects on weight and metabolic cytokines. *Support Care Cancer* 23, 2649-2654, doi:10.1007/s00520-015-2625-9 (2015).

9 Okamoto, H., Shono, K. & Nozaki-Taguchi, N. Low-dose of olanzapine has ameliorating effects on cancer-related anorexia. *Cancer Manag Res* 11, 2233-2239, doi:10.2147/CMAR.S191330 (2019).

10 Henry, F. E., Sugino, K., Tozer, A., Branco, T. & Sternson, S. M. Cell type-specific transcriptomics of hypothalamic energy-sensing neuron responses to weight-loss. *Elife* 4, doi:10.7554/eLife.09800 (2015).

11 Jiang, L. et al. Intracellular chloride channel protein CLIC1 regulates macrophage function through modulation of phagosomal acidification. *J Cell Sci* 125, 5479-5488, doi:10.1242/jcs.110072 (2012).

12 Campos, C. A. et al. Cancer-induced anorexia and malaise are mediated by CGRP neurons in the parabrachial nucleus. *Nat Neurosci* 20, 934-942, doi:10.1038/nn.4574 (2017).

13 Campos, C. A., Bowen, A. J., Schwartz, M. W. & Palmiter, R. D. Parabrachial CGRP Neurons Control Meal Termination. *Cell Metab* 23, 811-820, doi:10.1016/j.cmet.2016.04.006 (2016).

14 Roman, C. W., Derkach, V. A. & Palmiter, R. D. Genetically and functionally defined NTS to PBN brain circuits mediating anorexia. *Nat Commun* 7, 11905, doi: 10.1038/ncomms11905 (2016).

15 Michaelis, K. A. et al. Establishment and characterization of a novel murine model of pancreatic cancer cachexia. *J Cachexia Sarcopenia Muscle* 8, 824-838, doi:10.1002/jcsm.12225 (2017).

16 Averaimo, S., Milton, R. H., Duchen, M. R. & Mazzanti, M. Chloride intracellular channel 1 (CLIC1): Sensor and effector during oxidative stress. *FEBS Lett* 584, 2076-2084, doi:10.1016/j.febslet.2010.02.073 (2010).

17 Al Khamici, H. et al. Members of the chloride intracellular ion channel protein family demonstrate glutaredoxin-like enzymatic activity. *PLoS One* 10, e115699, doi:10.1371/journal.pone.0115699 (2015).

18 Goodchild, S. C., Angstmann, C. N., Breit, S. N., Curmi, P. M. & Brown, L. J. Transmembrane extension and oligomerization of the CLIC1 chloride intracellular channel protein upon membrane interaction. *Biochemistry* 50, 10887-10897, doi:10.1021/bi2012564 (2011).

19 Salao, K. et al. CLIC1 regulates dendritic cell antigen processing and presentation by modulating phagosome acidification and proteolysis. *Biol Open* 5, 620-630, doi: 10.1242/bio.018119 (2016).

Averaimo, S., Gritti, M., Barini, E., Gasparini, L. & Mazzanti, M. CLIC1 functional expression is required for cAMP-induced neurite elongation in post-natal mouse retinal ganglion cells. *J Neurochem* 131, 444-456, doi: 10.1111/jnc.12832 (2014).

21 Novarino, G. et al. Involvement of the intracellular ion channel CLIC1 in microglia-mediated beta-amyloid-induced neurotoxicity. *J Neurosci* 24, 5322-5330, doi: 10.1523/JNEUROSCI.1170-04.2004 (2004).

22 Gritti, M. et al. Metformin repositioning as antitumoral agent: selective antiproliferative effects in human glioblastoma stem cells, via inhibition of CLIC1-mediated ion current. *Oncotarget* 5, 11252-11268, doi:10.18632/oncotarget.2617 (2014).

23 Qiu, M. R. et al. Generation and characterization of mice with null mutation of the chloride intracellular channel 1 gene. *Genesis* 48, 127-136, doi:10.1002/dvg.20590 (2010).

24 Li, B. P. et al. CLIC1 Promotes the Progression of Gastric Cancer by Regulating the MAPK/AKT Pathways. *Cell Physiol Biochem* 46, 907-924, doi:10.1159/000488822 (2018).

Wang, L. et al. Elevated expression of chloride intracellular channel 1 is correlated with poor prognosis in human gliomas. *J Exp Clin Cancer Res* 31, 44, doi:10.1186/1756-9966-31-44 (2012).

26 Zhao, W., Lu, M. & Zhang, Q. Chloride intracellular channel 1 regulates migration and invasion in gastric cancer by triggering the ROS-mediated p38 MAPK signaling pathway. *Mol Med Rep* 12, 8041-8047, doi: 10.3892/mmr.2015.4459 (2015).

27 Barbieri, F. et al. Repurposed Biguanide Drugs in Glioblastoma Exert Antiproliferative Effects via the Inhibition of Intracellular Chloride Channel 1 Activity. *Front Oncol* 9, 135, doi:10.3389/fonc.2019.00135 (2019).

28 Wang, W. et al. Identification of Potent Chloride Intracellular Channel Protein 1 Inhibitors from Traditional Chinese Medicine through Structure-Based Virtual Screening and Molecular Dynamics Analysis. *Bio Med Res. Intl.*, doi.org/10.1155/2017/4751780 (2017).

What is claimed is:

1. A method of inhibiting appetite, hyperphagia, obesity, hunger or weight gain, reducing food intake, or inducing weight loss, in a subject comprising administering to a subject in need an effective amount of a chloride intracellular channel protein 1 (Clic1) inhibitor or antagonist, wherein the Clic1 inhibitor is not metformin.

2. The method of claim 1, wherein the Clic1 inhibitor decreases activity of Clic1.

3. The method of claim 2, wherein the Clic1 inhibitor is indanyloxyacetic acid 94 (IAA94) as defined below:

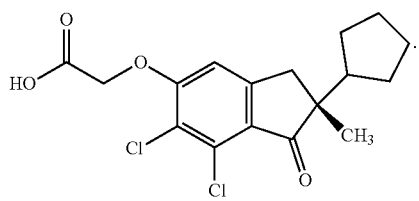 [SMILES: C[C@]1(C2CCCC2)Cc2cc(OCC(=O)O)c(Cl)c(Cl)c2C1=O]

4. The method of claim 2, wherein the Clic1 inhibitor is selected from compound 2, compound 14, compound 16, compound 20, compound 22, and compound 24 as defined below:

Compound 2

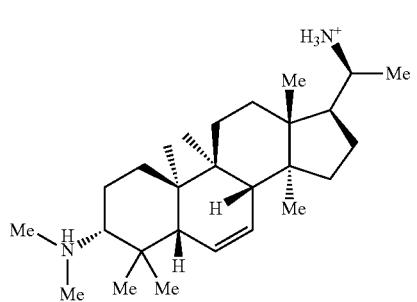

Compound 14

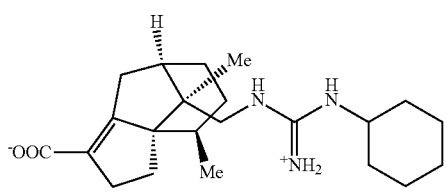

Compound 16

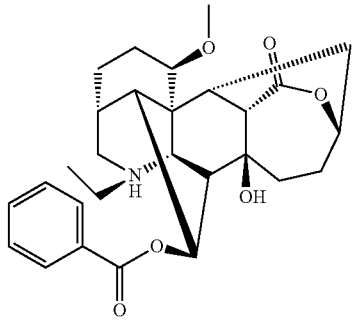

Compound 20

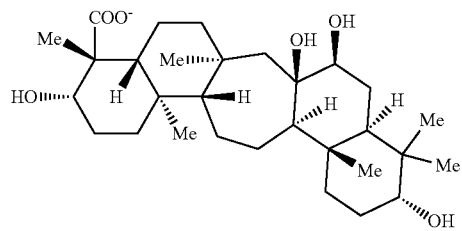

Compound 22

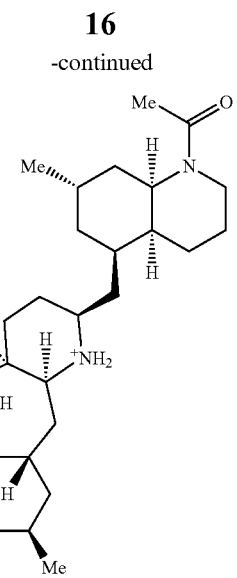

Compound 24

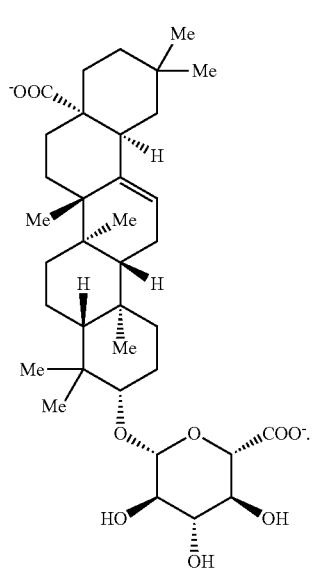

5. The method of claim 2, wherein the Clic1 inhibitor is compound 2 as defined below:

Compound 2

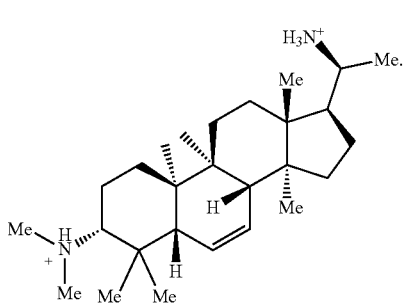

6. The method of claim 2, wherein the Clic1 inhibitor is compound 14, as defined below:

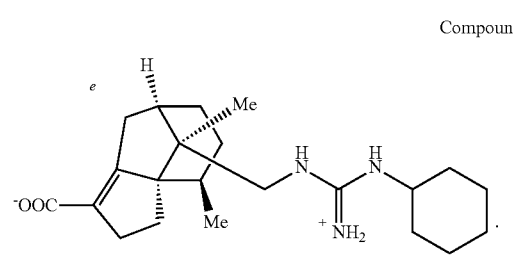

Compound 14

7. The method of claim 2, wherein the Clic1 inhibitor is compound 16 as defined below:

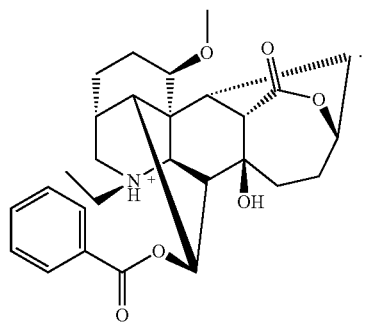

Compound 16

8. The method of claim 2, wherein the Clic1 inhibitor is compound 20 as defined below:

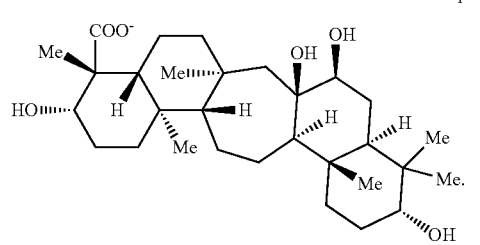

Compound 20

9. The method of claim 2, wherein the Clic1 inhibitor is compound 22 as defined below:

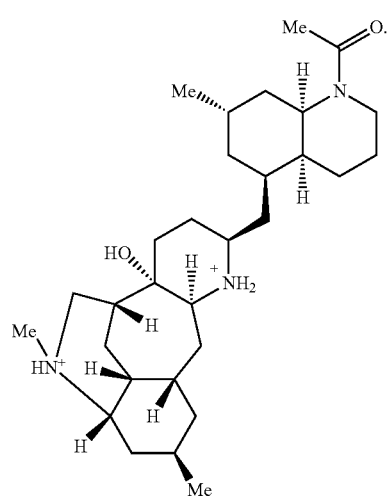

Compound 22

10. The method of claim 2, wherein the Clic1 inhibitor is compound 24 as defined below:

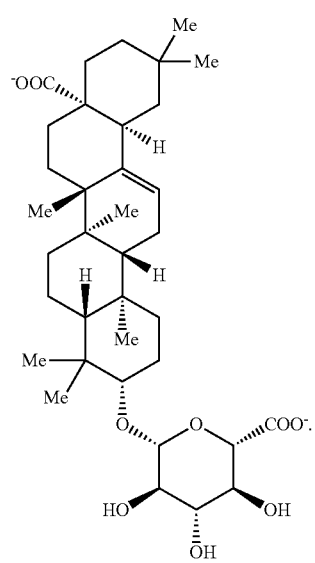

Compound 24

* * * * *